United States Patent [19]

Chang

[11] Patent Number: 5,942,233
[45] Date of Patent: Aug. 24, 1999

[54] HERBAL COMPOSITION FOR STIMULATING BLOOD CIRCULATION

[76] Inventor: Teh Shan Chang, 7F, No. 122, Sec. 1, Ho-Pi W. Rd., Taipei, Taiwan

[21] Appl. No.: 08/816,936

[22] Filed: Mar. 14, 1997

[51] Int. Cl.$^6$ .............................. A61K 35/78; A61K 9/70; A61K 47/26; A61K 47/38
[52] U.S. Cl. ...................... 424/195.1; 424/443; 424/447; 424/448; 514/778; 514/781; 514/782; 514/899
[58] Field of Search ................................ 424/195.1, 443, 424/447, 449, 485, 486, 488, 448; 514/777, 778, 779, 781, 782, 899

[56] References Cited

PUBLICATIONS

Yun–Wang Kao, Ed., "Mandarin Folk Prescriptions to Cure Diseases," vol. 2, Wangan Publishing Co., 1st edition, Taiwan, 1992.
Lawless, The Illustrated Encyclopedia of Essentials Oils, The Complete Guide to the Use of Oils in Aromatherapy and Herbalism, Barnes & Noble Books, p. 165, 1995.

*Primary Examiner*—Michael G. Wityshyn
*Assistant Examiner*—Janet M. Kerr
*Attorney, Agent, or Firm*—Smith, Gambrell & Russell; Beveridge, Degrandi, Weilacher & Young Intellectual Property Group

[57] ABSTRACT

This invention relates to an herb composition which comprises an amount of 30 to 45% by weight of one or more herbs for invigorating of blood circulation, an amount of 55 to 70% by weight of one or more herbs for excreting toxin from human body, and an amount of 0.5 to 4% by weight of one or more substances for keratin malacoma, all of which are based on the total weight of the composition, wherein the herb for invigorating of blood circulation is selected from the group consisting of *Prunnus persica*, south apricot kernel, white pepper (*Piper migrum*), glutinous rice (*Oryza sativa*) and white astragaluis (Common Bletillah Tuber); the herb for excreting toxin from human body is selected from the group consisting of *Cassiope stelleriana*, west carthamus (*Crocus sativus*), *Lonicera japonica*, rhubarb (*Rheum officinale*), *Bezoar bovis*, Liquorice powder (*Glycyrrhiza uralensis*), *Salvia multiorrhiza*, ligusticum (*Cnidium officinale*), *Momordica cochinchinensis*, achyranthes (*Achyrathes bidentata*) and astragalus (*Astragalus hiroshimanus*); and the substance for keratin malacoma is selected from the group consisting of vinegar, acetate salt, Szechwan notoginseng and *Rehmannia glufinosa*. This invention also relates to a paste containing the present herb composition which is produced by mixing the herb composition with vinegar, water or wine and optionally a binder. The paste is useful for reestablishing of vital energy, invigorating of blood circulation and elimination of blood stasis and for cold remedy by applying the paste on the sole of the human's foot.

9 Claims, No Drawings

HERBAL COMPOSITION FOR STIMULATING BLOOD CIRCULATION

FIELD OF THE INVENTION

This invention provides an herb composition and an herbal plaster made from the same to be applied to the sole of human's foot to communicate and activate channels and collaterals, to strengthen body resistance and eliminate pathogenic factors, and to promote the flow of vital energy and blood.

BACKGROUND OF THE INVENTION

With the increase of age, human's physical condition as well as physiological condition always deteriorate. The aged people thus become less resistant to pathogens and less adaptive to sudden weather-change. The most important thing to keep them healthy is to increase the resistance and promote the adaptivity. Although the medical societies in all countries have been making efforts on this direction and have developed a variety of medicines, prescriptions including single and compound formulae, and dosages including oral, parenteral and suppository forms; however, synthetic processes for manufacturing such medicines are complicated and side effects of these medicines such as gastroentelic and hepatic damages sometimes occur. Therefore, those medicines are not as satisfactory as desired.

The arteriosclerosis is especially one of the most common diseases which occur during human aging process. When human gets older, the incidences of arteriosclerosis become higher. Generally, aortosclerosis and coronary arteriosclerosis come first, then cerebral arteriosclerosis occurs. If the patients suffer from hypertension simultaneously, it is even dangerous for the occurrence of cerebral hemorrhage and cerebral thrombosis. From the medical investigation, it is shown that the arteriosclerosis is the major factor causing the death of elderly people. Cardiovascular and cerebral vascular diseases make the major leading causes of death in Taiwan and the arterioscleros is by far an important factor causing such diseases.

Hyperlipemia is also a critical factor causing atherosciero-sistic cardiac diseases. The reduction of Hyperlipemia can not only prevent apoplexy and hemiparalysis, but also prolong human's life. Therefore, to reduce the incidences of apoplexy and hemiparalysis, the occurrence and development of arteriosclerosis should be prevented and the study should be focused on lowering the level of lipid in blood.

The investigation also shows basically hypertension and arteriosclerosis are two main causes for the incidence of hemiparalysis. Among them, 80% of hemiparalysis are caused by hypertension and such hemiparalysis often occurs on elderly people. The hypertension is a chronic disease and always induces arteriosclerosis. The reason is that hypertension may cause higher tension of blood vessels and such a tension will act on endoaorterium to break elastic fiber of the vessels and damage the endoaorterium, thereby affects the permeability of blood vessels and the transportation of nutrients. The hypertension further easily induces the breakage of the capillaries and also induces the bleeding from the endoaorterium to form blood clots. Since the composition of the blood is changed, cholesterol and triglyceride in blood increase and cause arteriosclerosis.

When human suffering from hypertension, the thickening of blood vessels and the interaction of lipids in blood will cause the deposition of lipids on inside wall of the artery. The arterial wall will become thick hard and fragile, thereby losts its elasticity. When blood pressure suddenly increases, and the fragile arterial wall can no longer bear on it, the arterial wall will break and the bleeding occurs. The bleeding occuring on cerebrovasculum is called cerebral hemorrhage. If a patient suffering from hypertension is not properly treated, cerebral apoplexy most easily occurs and causes herniparalysis.

For patients suffering from hypertension, cerebral arteriosclerosis or abnormal hemodynamics, symptoms such as dizziness, ocula vertigo, and paralysis of thumb and forefinger always occur. An approach on how to notice these, symptoms in advance is studied and developed by those skilled in the medical field. Generally, in Chinese medicine, it is considered that plump persons who take high lipid-containing food frequently suffer from hemiparalysis easily. The occurrence of such hemiparalysis is attributed to deficiency of vital energy and formation of blood stasis. Furthermore, it is also attributed to clogging of channels and collaterals.

The process for preparing drugs or preparations for treating such diseases, however, is complicated and the side effects such as gasteroenteric and hepatic damage problems may occur after the administration. Drugs and preparations which are as satisfactory as desired have not been found yet.

While considering the danger of surgical removement of thrombus in the brain of a patient stuffering from apoplexy, the inventor has studied ancient literatures and done research based on the knowledge that a transdermic treatment is a safer method, and has invented in accordance with principles of Chinese medicine an herbal composition for middle-aged and elderly people to prevent apoplexy and cardiovascular thrombosis disorders, to decrease cholesterol to communicate channels and collaterals (to relieve soreness of muscle), to remove toxin from human body, to relieve lassitude and depression of spirits, to cure canes, athlete's foot, irregular menstruation, paralysis of limbs, and frozen shoulder.

Actually, the above diseases are fundamentally the same pathogenesis and all of them result from the obstruction of blood circulation and the accumulation of toxin in human body. With an herb composition for external application, instead of orally administration, the drug is transcutaneously delivered into human body. Side effects such as gasteroenteric and hepatic damage problems can be avoided. Because of its simplicity, safety and exact therapeutic effects, the transcutaneous treatment is a practical method.

When the herb composition is formulated into a paste, it can be applied to specific areas of human's skin or to an area corresponding to the organ to be treated. This external treatment is an important method for treating common diseases, chronic diseases, multiple diseases and intractable diseases.

The herbal paste as mentioned above is usually applied to human's skin in optional areas depending on various kinds of diseases to be treated. In general, the herbal paste is applied to human's skin in lower position if the focus locates at upper part of body, and vice visa. The herbal paste is also applied to human's skin for treating internal injury or directly applied to injured area. This transcutaneous treatment with herbal paste is an ancient teating method. In "Ben Tsao Gang Mu" (The name of a book in which about 1,000 plants and about 500 animals of medicinal value were listed. It was edited by Shih-Chen Lee during Ming dynasty in China), it is stated that "Raw aconite is ground and mixed with green onion juice to form a paste, and applied to Point Yungchuan (an acupuncture point located at the sole of the feet) to cure nose diseases.". Therefore, it has been used for quite a long time.

The reason for applying herbal paste to specific areas of human's skin or to an area corresponding to the organ to be treated is that there are many acupuncture points distributing over human's skin. It is well known that the acupuncture points corresponding to all organs are found at the sole of the feet, therefore the sole massage and/or kneading could attain certain therapeutic effects. However, the sole massage and/or kneading is a physicotherapy, it could only temporarily relieve the pain and could not attain exact therapeutic effects.

This invention provides an herb composition for external application, which is prepared by grinding certain herbs into powder, then the powder is formulated into an herbal paste. When the herbal paste is applied to specific areas of human's skin or to an area corresponding to the organ to be treated, the herb composition is absorbed via pores of the skin and easily delivered into human body through dermis. 90% of the dermis are connective tissues which comprise plenty of blood vessels, therefore the dermis play an important role to deliver the drug into the body. In those areas of treatment, for example, there are numbers of hair follicles of high permeability at Point Paihui (the acupuncture point located at the top of the skull), therefore it is advantageous to the absorption of the drug. Besides, the keratin layers in the skin of hands and feet are thinner, so they are the areas where the drug is easily absorbed. Furthermore, the acupuncture points distribute all over the channels and collaterals in human body. The channels and collaterals connect outwardly with the skin and inwardly with all the organs. They constitute the integral part and the unique system to communicate the whole human body. Therefore, being absorbed through the skin, the acupuncture points, and the channels and collaterals, the herb composition of the invention can develop its effects and cure the diseases.

SUMMARY OF THE INVENTION

The present invention provides an herb composition which comprises: 30 to 45% by weight of one or more blood circulation promoting herbal materials selected from the group consisting of peach kernel, southern apricot kernel white pepper, glutinous rice and white astragalus; 55 to 70% by weight of one or more toxin removing herbal materials selected from the group consisting of *Cassiope stelieriana*, safflower, Japanese honeysuckle flower, rhubarb, cow bezoar, liquorice powder, red sage root, ligusticum *Momoridca cochinchinensis*, achyranthes root and astragalus root; and about 0.5 to 4% by weight (based on total weights of preceding ingredients) of one or more keratin layers softening substances selected from the group consisting of vinegar, acetates, raw rehmannia root and notoginseng. After all the ingredients are mixed and ground, a binder is optionally added, the mixture is combined with solvents such as vinegar, water or wine to form an herbal paste for applying to the sole of human's foot to communicate and activate channels and collaterals, to strengthen body resistance and eliminate pathogenic factors, and to promote the flow of vital energy and blood.

DETAILED DESCRIPTION OF THE INVENTION

In order to prepare the herb composition of the invention, the inventor has studied various traditional Chinese medicine books. Those herbs which give functions to communicate and activate the channels and collaterals, to strengthen body resistance and eliminate pathogenic factors, and to promote vital energy and blood circulation, are screened. Sonic of them are given in the following:

Peach kernel (*Prunnus persica*): the action of it is to remove blood stasis and to lubricate the intestines. It is suitably used for patients with blood stasis, dysmenorrhea, amenorrhea, fractures and injuries.

Glutinous rice: it helps to clear away the toxin and remove the pus. It is glutinous when ground into powder and is suitable to be prepared as a paste.

White pepper: it regulates the circulation of vital energy and removes the phlegm, and also directs the medicine to the right channel. While coordinating with blood stasis removing functions of peach kernel and the safflower, it clears away toxin from the body.

Southern apricot kernel: southern apricot kernel also regulates the circulation of vital energy and removes the phlegm. In addition, it helps to sweat and has the same function as cinnamon twig and white pepper as to direct the medicine to the right channel. When southern apricot kernel coordinates with peach kernel and safflower, toxin is cleared away from the body as sweat.

Among them, peach kernel, glutinous rice and white pepper have been described as the components of a folk prescription for treating hypertension on page 4 in "Mandarin Folk Prescriptions to Cure Serious Diseases", vol. 2, edited by Yun-Wang Kao, Wangan Publishing Co., 1st edition in Taiwan (1992). The function of promoting blood circulation to fulfill partial anti-hypertensive effect is mentioned. However, on the same page, it is also mentioned that "the components contained in the folk prescription are ground into powder, then mixed with egg albumen to form thin cake; the cake is applied to the sole of the foot and wrapped with gauze bandage; next morning, take off the cake and examine the sole; if blue color appears on the sole, it means that blood pressure has already been decreased; repeat this treatment for 5 days as one therapeutic process". From this disclosure, the inventor has found that although such a folk prescription renders the effects of promoting blood circulation and treating hypertension, a blue-violet color will appear on the sole of the foot. It is unpleasant, especially for women wearing high-heeled shoes. The blue-violet color appearing on the sole results from the accumulation of toxin removed by the herbs. Also, a few red blisters are found on the skin of the sole, which are similar to athlete's foot. The blisters are attributed to the toxin delivering together with blood to peripheral nerves in toes. If peripheral nerves perform good function, the toxin will be removed as blisters; if peripheral nerves do not perform the function, the toxin could not be removed and will cause a pain in the sole. Such a symptom occurs on a patient suffering from diabetes, hypertension and other chronic diseases.

In view of this, the present invention provides an herb composition which, in addition to the herbs for promoting blood circulation, also comprising herbs for removing toxin from human body, and substances for softening keratin layers The herb composition of the invention is combined with solvents such as vinegar, water or wine, and optionally, a binder, to form an herbal paste for external application.

In order to completely remove toxin from human body, the inventor has studied intensively and the herbs as follows were screened: safflowers (*Crocus sativus*), rhubarb (*Rheum officinale*), red sage root (*Salvia multiorrhiza*), ligusticum (*Cnidium officinale*), *Momordica cochinchinensis*, achyrantlies root (*Achyranthes bidentata*), and astragalus root (*Astragalus hiroshinianus*). When they are added to the herb composition of the invention, the amount used is about 20% to about 60% by weight based on the total weight of the herb composition. As to the individual effect of these toxin removing herbal materials, for example, astragalus root can invigorate vital energy and replenish "yang", relieve exterior syndrome, induce dieresis to alleviate edema, and remove the pus. In addition, it has dual regulatory effects to blood pressure, that is, decreasing blood pressure for hypertension and increasing blood pressure for hypertension.

The pharmacological actions of the other herbs are as follows:

Safflowers: The main functions are to remove blood stasis, to alleviate edema, to relieve pain and to regenerate fresh blood.

Red sage root: It helps to enrich the blood. Meanwhile, it may expand blood vessels and obviously helps to improve the circulation barrier in blood stasis.

These toxin removing herbal materials used in the herb composition of the invention generally are suitable as servant herbs and may additionally include, for example, *Talinum crassifolium*, liquorice, Japanese honeysuckle flower and *Cassiope stelleriana*. Among them, liquorice is often used in the prescriptions to improve vital energy and remove toxin. Japanese honeysuckle flower renders the effects of eleminating fever, removing toxin, curing ulcers and scabies, and nourishing the blood. The amount of servant herbs used is about 30% by weight based on the total weight of the herb composition. Further, the liquortice may be added to the herb composition in the amount of about 1 to 10% by weight so that the total amount of servant herbs used reaches about 40% by weight of the herb composition. The amount of each herb used in the herb composition of the invention can be varied depending on the required pharmacological effects.

When using these toxin removing herbal materials, and combining with keratin layers softening substances such as vinegar, acetates, dried relimannia root (*Rehmannia glufinosa*) and notoginseng, the blood circulating function of the herb composition of the invention is promoted; the toxin is removed smoothly; many synergistic effects occur. Moreover, to form an herbal paste, the herb composition of the invention is formulated with vinegar, water or wine, instead of egg albumin used in the above mentioned folk prescription. It would not give much trouble. The blue-violet color would not appear on the sole either.

Therefore, one object of the invention is to provide an herb composition which comprises: 30 to 45% by weight of one or more blood circulation promoting substances selected from the group consisting of peach kernel, southern apricot kernel, white pepper, glutinous rice and white astragalus; 55 to 70% by weight of one or more toxin removing substances selected from the group consisting of *Cassiope stelleriana*, safflower, Japanese honeysuckle flower, rhubarb, cow bezoar, liquorice powder, red sage root, ligusticum, *Momoridca cochinchinensis*, achyranthes root and astragalus root, and one or more keratin layers softening substances selected from the group consisting of vinegar, acetates, raw relmannia root and notoginseng. After all the ingredients are mixed and ground, an binder is optionally added, the mixture is combined with solvents such as vinegar, water or wine to form an herbal paste for external application.

Further, the amount used and the functions of some of the ingredients are described in detail in the following:

Peach kernel: The amount used is about 10 to 30% by weight. If the amount is less than 10% by weight, the effect of removing blood stasis is not significant.

Safflower: The amount used is about 3 to 15% by weight.

Glutinous rice: The amount used is about 0.4 to 1.2% by weight.

White pepper: The amount used is about 0.4 to 1.2% by weight.

Southern apricot kernel: When coordinating with cinnamon twig and white pepper, the total amount of them is about 10 to 30% by weight of the herb composition; when coordinating with peach kernel, the total amount of them is more than about 25% by weight of the herb composition.

Vinegar and acetates: Usually, edible vinegar is used. The purpose is to soften keratin layers (callus) of the sole, so the drug can be easily absorbed. The main component of vinegar is acetic acid, normally it is in liquid state. Acetates such as sodium acetate, potassium acetate and calcium acetate arc also suitable to be used in the herb composition of the invention. These acetates arc powdery solids, which can be directly blended with the herb composition, mixed with water or other liquid carriers (for example, wine), and formulated into herbal paste for external application Binders: For the folk prescription mentioned above, it gives much trouble to be mixed with egg albumin to form thin cake right before using. The herb composition of the invention may be incorporated in advance with about 0.5 to 2.0% by weight of binders in dry powdery form. Suitable binders are, for example, synthetic water-soluble polymers such as sodium polyacrylate, polyacrylic acid, polyvinyl alcohol, polyvinyl pyrrolidone, naturally occurring polymers such as arabic gum, starch, egg albumin and gelatin, methyl cellulose, hydroxypropyl cellulose, sodium carboxymethyl cellulose, alginic acid, sodium alginate, ammonium algiate and the like.

Wine: Rice wine is generally used in the herb composition, optionally other kinds of wines are also suitable. The wine renders not only the effect of blending each ingredient but also the effect of accelerating the transportation of active ingredients.

The herb composition of the invention is formulated into herbal paste. Instead of orally administration, the drug is trnascutaneously delivered into human body. Side effects such as gasteroenteric and hepatic damage problems can be avoided. Because of its simplicity, safety and exact therapeutic effects, it is a practical method.

Furthermore, the herb composition of the invention may be formulated into an herbal plaster, that is, the herb composition may be formulated into a transdermic therapeutic system to be applied to the skin. The system comprises a covering layer which prohibits the penetration of active ingredients; a pressure-sensitive adhesive layer (plaster bases as described hereinafter); and optionally, a releasable protecting layer. The herbal plaster is prepared by grinding the herb composition to form a powdery mixture, formulated the powdery mixture with liquid carriers to form a paste, blending the paste with plaster bases, applying the blend to a woven or non-woven fabric, and finally covering with a covering layer.

The plaster bases comprise one or more binders selected from the group consisting of synthetic water-soluble polymers (such as sodium polyacrylate, polyacrylic acid, polyvinyl alcohol, polyvinyl pyrrolidone, polyethylene oxide, polyvinyl acrylate and the like), naturally occurring polymers (such as arabic gum, starch, gelatin and the like), methyl cellulose, hydroxypropyl cellulose, alginic acid, sodium alginate, ammonium alginate and sodium carboxymethyl cellulose; one or more wetting agents selected from the group consisting of urea, glycerol, propylene glycol, butylene glycol and glucosyl alcohol; one or more fillers selected from the group consisting of kaolin, zinc oxide, talc, titanium white, bentonite and epoxy resins; one or more organic acid salts selected from the group consisting of calcium, magnesium and aluminum salts of citrate, tartrate, maleate, maleic anhydride and succinate; water; one or more solubilizers selected from the group consisting of propylene carbonate and diisopropyl adipate; one or more adhesive agents selected from the group consisting of rosin, ester gum, polybutylene and polyacrylate; one or more contact dermatitis preventing agents selected from the group consisting of chloroaniline maleate, glycyrrhizn and adrenal cortical hormone; and one or more additives selected from the group consisting of salicylic acid, methyl salicylate, glycol salicylate, 1-menthol, camphor, vanitlylamide nonanate, daphne phenol, capsaicin and peppermint oil.

Moreover, the herb composition of the invention may be formulated into an herbal emplastrum. The bases for an emplastrum comprise well-known polymer bases (such as methacrylates, the acrylatcs composition of copolymers of vinyl monomer and acrylotitriles, vinyl acetates, vinyl propionates and the like; silicone resin, polyisoprene rubber, polyisobutylene gun, natural gum, acrylate rubber, styrene-butadiene-styrene block copolymer, styrene-isoprene-styrene block copolymer and the like), oils and fiats or higher fatty acids (such as almond oil, olive oil, camellia oil, peanut oil, oleic oil, paraffin, polybutylene and the like), adhesive agents (such as rosin, rosin modified maleates, hydrorosinate and the like), and suitably selected contact dermatitis preventing agents and, optionally, other additives such as camphor, 1-menthol, daphne phenol, vanillyamide nonanate, capsaicin and peppermint oil. The herbal emplastrum is prepared by blending the herb composition with bases for an emplastrum to form a homogeneous blend, spreading the blend on a supporter (such as flexible or non-flexible cloth, non-woven fabric or paper and the like) in conventional manner, and then covering with a releasable covering layer suitably selected from polyethylene, polypropylene, polyvinyl chloride, polyester, polyvinylidene chloride, silicone processed paper and the like.

The herb composition of the invention is useful for treating and preventing hypertension and apoplexy, because the ingredients of the composition exhibit synergistic therapeutic effects and remove toxin from human body. Many specialists have proved that a patient suffering from hypertension or apoplexy is always accompanied with cerebral thrombosis which will cause abnormal hemodynamics. The abnormal hemodynamics may be indicated by the increase of viscosity of whole blood, the increase of hemoglobin, the slowness of electrophoretic mobility of platelet and hemoglobin, the increase of the amount of fibrinogen, agglutination of platelet and increasing of adhesivity of platelet. The abnormal hemodynamics in the patient will cause "concentrated, viscous, condensed and gathered" blood clots. Experiments for comparing the hemodynamics of a patient treated by the herb composition of the invention (as treatment group) with that of the patient before the treatment (as control group) are carried out. The examined items arc as mentioned above and include the viscosity of whole blood, the agglutination index of hemoglobin, the concentration of hemoglobin, the amount of fibrinogen, the agglutination ratio of platelet and the adhesivity ratio of platelet. Generally, the treatment group shows the results of decreased viscosity of blood, less agglutination of hemoglobin, reduced amount of fibrinogen, less agglutination ratio of platelet and reduced adhesivity of platelet. The decrease of the viscosity of blood may also be easily demonstrated by an experiment in which drops of blood taken from the finger of a patient before and alter the treatment are dropped into water, and the blood after treatment diffuses rapidly. On the other hand, from the indication of thinning of keratin layers on the sole of foot, it is also shown that toxin had been removed from human body via the sole. Moreover, the herb composition of the invention is suitable for women suffering from menoxenia and/or dysmenorrhea. This is shown by the effusion of great amount of black blood stasis after treatment.

EXAMPLES

The present invention will be described in detail by following examples without limiting the scope of the invention. The weight % used in the examples is based on total weight of the herb composition unless otherwise stated.

Example 1

16.0% by weight of peach kernel, 0.8% by weight of glutinous rice, 1.0% by weight of white pepper, 12.0% by weight of southern apricot kemel, 1.2% by weight of white astragalus, 15.0% by weight of *Cassiope stelleriana*, 10.0% by weight of safflower, 5.0% by weight of Japanese honeysuckle flower, 6.0% by weight of rhubarb, 5.0% by weight of liquorice powder, 4.5% by weight of red sage root 5.0% by weight of ligusticum, 7.0% by weight of *Momordica cochinchinensis*, 3.5% by weight of achyranthes root, 6.0% by weight of astragalus root, and 2.0% by weight of sodium acetate were ground into powdery mixture. To the mixture, 3.0% by weight (based on total weight of preceding ingredients) of egg albumin powder was added. Then, water was gradually added to 100 grain of resulting powdery mixture with stirring to form paste. The paste was applied to thee sole of patients suffering from hypertension and wrapped with a supporter (selected from flexible or non-flexible cloth, non-woven fabric, non-woven paper, polyethylene, polypropylene, polyvinyl chloride, polyvinylidene chloride, processed paper and the like) overnight (approximately 8 to 10 hours). After removing the paste and cleaning, it was shown that keratin layers under the sole were softened and could be scraped off. The skin on the sole became smoother and blood pressure of the patient was decreased.

Example 2

14.0% by weight of peach kernel, 1.0% by weight of glutinous rice, 1.0% by weight of white pepper, 18.0% by weight of southern apricot kernel, 1.0% by weight of white astragalus 20.0% by weight of *Cassiope stelleriana*, 15.0% by weight of safflower, 3.0% by weight of liquorice powder, 8.0% by weight of red sage root, 6.0% by weight of ligusticum, 2.0% by weight of *Momordica cochinchinensis*, 3.0% by weight of achyranthes root, 4.0% by weight of astragalus root, and 4.0 by weight of notoginseng were ground into powdery mixture. Edible vinegar was gradually added to 100 gram of the mixture with stirring to form paste. The paste was applied to the sole of female patients suffering from dysmenorrhea and wrapped with a supporter overnight (approximately 8 to 10 hours). After removing the paste and cleaning, it was shown that keratin layers under the sole were softened and could be scraped off. The skin on the sole became smoother and black menstrual blood stasis was effused from the body. The mentrulation has been regulated.

Example 3

17.0% by weight of peach kernel 0.4% by weight of glutinous rice, 1.0% by weight of white pepper, 25.0% by weight of southern apricot kernel, 0.6% by weight of white astragalus 8.0% by weight of *Cassiope stelleriana*, 7.0% by weight of safflower, 9.0% by weight of rhubarb, 0.5% by weight of cow bezoar, 7.5% by weight of liquorice powder, 8.0% by weight of red sage root 3.0% by weight of ligusticum, 5.0% by weight of *Momordica cochinchinensis*, 6.0% by weight of achyranthes root and 2.0% by weight of astragalus root were ground into powdery mixture. To the mixture, 2.0% by weight (based on total weight of the preceding ingredients) of sodium alginate was added. Then, 10.0 ml of edible vinegar and rice wine were gradually added to 100 gram of resulting powdery mixture with stirring to form paste. The paste was applied to the sole of patients suffering from frozen shoulder and wrapped with a supporter overnight (approximately 8 to 10 hours). After removing the paste and cleaning, it was shown that keratin layers under the sole were softened and could be scraped off. The skin on the sole became smoother and the patients have not suffered from frozen shoulder any more.

Example 4

The amounts used in this example were based on total weight of the finished plaster. 10 to 50% by weight of any powdery mixture prepared from examples 1 to 3 was mixed and dissolved in 0.5 to 8% by weight of isopropyl adipate (as solubilizers) to form a homogeneous mixture. Separately, 5 to 20% by weight of sodium carboxymethyl cellulose (as binders) was dispersed in 5 to 40% by weight of glycerol (as wetting agents), and 10 to 80% by weight of water and 10% by weight of zinc oxide and talc (as fillers) were added thereto. The homogeneous mixture was blended with the latter mixture to form a homogeneous blend. The blend was spread on a supporter in conventional manner, and covered with a releasable covering layer to obtain a plaster for applying to the sole of the foot.

What is claimed is:

1. An herbal composition comprising:

30 to 45% by weight of a first herbal material comprising about 16% by weight peach kernel, about 12% by weight southern apricot kernel, about 1% by weight white pepper, about 0.8% by weight glutinous rice and about 1.2% by weight white astragalus;

55 to 70% by weight of a second herbal material comprising about 15% by weight *Cassiope stelleriana*, about 10% by weight safflower, about 5% by weight Japanese honeysuckle flower, about 6% by weight rhubarb, about 5% by weight liquorice powder, about 4.5% by weight red sage root, about 5% by weight ligusticum, about 7% by weight *Momordica cochinchinensis*, about 3.5% by weight achyranthes root and about 6% by weight astragalus root; and about 0.5 to 4% by weight, based on the total weight of the first and second herbal materials, of a keratin softening substance comprising about 2% by weight sodium acetate.

2. An herbal composition comprising:

30 to 45% by weight of a first herbal material comprising about 14% by weight peach kernel, about 18% by weight southern apricot kernel, about 1% by weight white pepper, about 1% by weight glutinous rice and about 1% by weight white astragalus;

55 to 70% by weight of a second herbal material comprising about 20% by weight *Cassiope stelleriana*, about 15% by weight safflower, about 3% by weight liquorice powder, about 8% by weight red sage root, about 6% by weight ligusticum, about 2% by weight *Momordica cochinchinensis*, about 3% by weight achyranthes root and about 4% by weight astragalus root; and about 0.5 to 4% by weight, based on the total weight of the first and second herbal materials, of a keratin softening substance comprising about 4% by weight notoginseng.

3. An herbal composition comprising:

30 to 45% by weight of a first herbal material comprising about 17% by weight peach kernel, about 25% by weight southern apricot kernel, about 1% by weight white pepper, about 0.4% by weight glutinous rice and about 0.6% by weight white astragalus;

55 to 70% by weight of a second herbal material comprising about 8% by weight *Cassiope stelleriana*, about 7% by weight safflower, about 9% by weight rhubarb, about 0.5% cow bezoar, about 7.5% by weight liquorice powder, about 8% by weight red sage root, about 3% by weight ligusticum, about 5% by weight *Momordica cochinchinensis*, about 6% by weight achyranthes root and about 2% by weight astragalus root; and about 0.5 to 4% by weight, based on the total weight of the first and second herbal materials, of a keratin softening substance comprising about 10 ml of vinegar.

4. A method of improving blood circulation in a patient comprising:

applying to the skin of a patient in need thereof, the herbal composition of claim 1.

5. A method of improving blood circulation in a patient comprising:

applying to the skin of a patient in need thereof, the herbal composition of claim 2.

6. A method of improving blood circulation in a patient comprising:

applying to the skin of a patient in need thereof, the herbal composition of claim 3.

7. An herbal plaster having a pressure sensitive layer comprising the herbal composition of claim 1 and a plaster base.

8. An herbal plaster having a pressure sensitive layer comprising the herbal composition of claim 2 and a plaster base.

9. An herbal plaster having a pressure sensitive layer comprising the herbal composition of claim 3 and a plaster base.

* * * * *